(12) United States Patent
Scheffler

(10) Patent No.: US 8,536,380 B2
(45) Date of Patent: Sep. 17, 2013

(54) TRITERPENE-CONTAINING OLEOGEL-FORMING AGENT, TRITERPENE-CONTAINING OLEOGEL AND METHOD FOR PRODUCING A TRITERPENE-CONTAINING OLEOGEL

(75) Inventor: Armin Scheffler, Niefern-Öschelbronn (DE)

(73) Assignee: Birken GmbH, Niefern-Öschelbronn (DE)

( * ) Notice: Subject to any disclaimer, the term of this patent is extended or adjusted under 35 U.S.C. 154(b) by 552 days.

(21) Appl. No.: 11/630,180

(22) PCT Filed: Jun. 21, 2005

(86) PCT No.: PCT/EP2005/006710
§ 371 (c)(1),
(2), (4) Date: Jun. 8, 2007

(87) PCT Pub. No.: WO2005/123037
PCT Pub. Date: Dec. 29, 2005

(65) Prior Publication Data
US 2007/0299285 A1   Dec. 27, 2007

(30) Foreign Application Priority Data
Jun. 22, 2004 (DE) .......................... 10 2004 030 044

(51) Int. Cl.
*A61K 9/14* (2006.01)
*A61K 9/10* (2006.01)
*C07C 35/44* (2006.01)
*C07C 35/42* (2006.01)
*C07J 53/00* (2006.01)
*C07J 75/00* (2006.01)

(52) U.S. Cl.
CPC ................. *C07C 35/42* (2013.01); *C07J 53/00* (2013.01); *C07J 75/00* (2013.01)
USPC .......................................... 568/714; 552/510

(58) Field of Classification Search
USPC ........................................................ 552/510
See application file for complete search history.

(56) References Cited

U.S. PATENT DOCUMENTS

| | | | |
|---|---|---|---|
| 4,933,177 A | 6/1990 | Grollier et al. | |
| 5,750,578 A | 5/1998 | Carlson et al. | |
| 6,187,323 B1 * | 2/2001 | Aiache et al. | 424/401 |
| 6,403,816 B1 * | 6/2002 | Jaggi et al. | 552/510 |
| 2001/0038878 A1 | 11/2001 | Bhaggan et al. | |
| 2002/0119935 A1 | 8/2002 | Krasutsky et al. | |
| 2002/0128210 A1 | 9/2002 | Krasutsky et al. | |
| 2003/0087789 A1 * | 5/2003 | Scheffler | 510/417 |
| 2003/0124158 A1 | 7/2003 | Heidenfelder et al. | |

FOREIGN PATENT DOCUMENTS

| | | |
|---|---|---|
| DE | 3207005 A1 | 9/1982 |
| DE | 10056902 A1 | 5/2002 |
| EP | 1 410 790 A1 | 4/2004 |
| JP | H05-004911 | 1/1993 |
| JP | 2002-138014 | 5/2002 |
| JP | 2003-146865 | 5/2003 |
| JP | 2003-335627 | 11/2003 |
| JP | 2004-107227 | 4/2004 |
| JP | 2004519411 | 7/2004 |
| JP | 2005004911 | 1/2005 |
| WO | WO 98/34603 | 8/1998 |
| WO | WO 00/62751 | 10/2000 |
| WO | WO 01/03712 | 1/2001 |
| WO | WO 01/72315 A1 | 10/2001 |
| WO | WO01/72315 A1 | 10/2001 |
| WO | WO 03/043594 A2 | 5/2003 |
| WO | WO 2004/016336 A1 | 2/2004 |

OTHER PUBLICATIONS

Wheeler, "Preparation of Betulin by Sublimation", Pharmaceutical Journal, Nov. 25, 1899.
Shrikhande B.K. et al., "Development and Evaluation of Anti-Inflammatory Oleogels of *Bosewellia serrata* (Gugel) and *Curcuma longa* (Turmeric)", Indian Drugs 38(12) Dec. 2001, pp. 613-616.
Knop, von Klaus et al., "Colloidal Silicas as gel-forming agents", GOVI Verlag (GOVI publishers), 2001.
Yasukawa, K. et al., "Sterol and Triterpene Derivatives from Plants Inhibit the Effects of a Tumor Promoter, and Sitosterol and Betulinic Acid Inhibit Tumor Formation in Mouse Skin Two-Stage Carcinogenesis", College of Pharmacy, Nihon University, Chiba, Oncology 1991; 48:72-76.
Recio, Maria del Carmen, "Investigations on the Steroidal Anti-Inflammatory Activity of Triterpenoids from *Diospyros leucomelas*", Planta Med. 61 (1995) 9-12.

* cited by examiner

*Primary Examiner* — Rosalynd Keys
(74) *Attorney, Agent, or Firm* — Muirhead and Saturnelli, LLC

(57) ABSTRACT

The invention relates to an oleogel-forming agent which comprises at least one highly dispersed triterpene. The invention also relates to an oleogel which comprises a nonpolar liquid in an amount ranging from 80% by weight to 99% by weight based on the total weight of the oleogel and an oleogel-forming agent comprising a highly dispersed triterpene in an amount ranging from 1% by weight to 20% by weight based on the total weight of the oleogel. The invention also relates to a method for producing an oleogel.

10 Claims, 1 Drawing Sheet

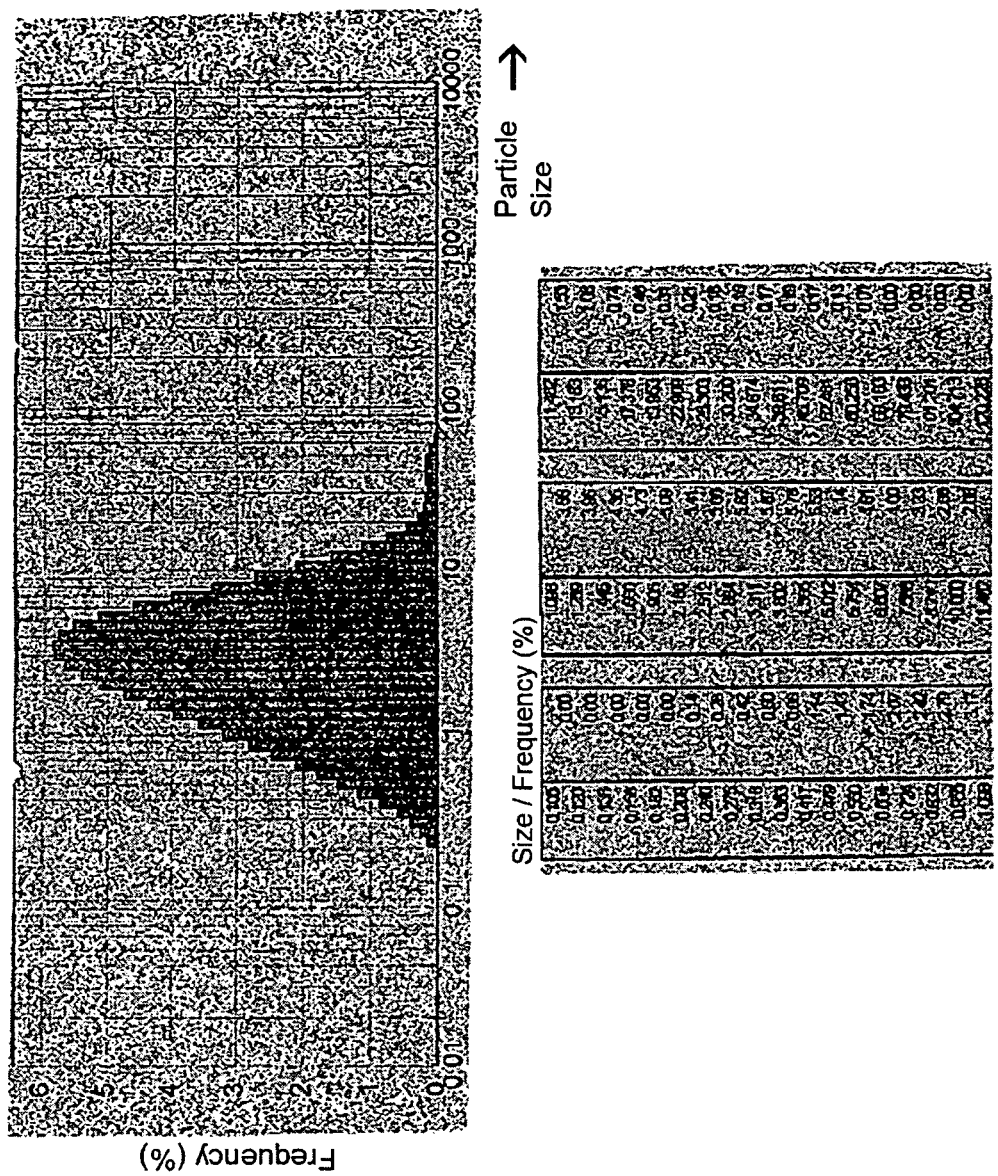

TRITERPENE-CONTAINING OLEOGEL-FORMING AGENT, TRITERPENE-CONTAINING OLEOGEL AND METHOD FOR PRODUCING A TRITERPENE-CONTAINING OLEOGEL

TECHNICAL FIELD

The present invention relates to an oleogel-forming agent, an oleogel having this gel-forming agent and a method for producing an oleogel.

BACKGROUND OF THE INVENTION

Gels are finely dispersed systems of a liquid and a solid phase in which the solid phase forms a contiguous three-dimensional structure and the two phases are thoroughly intermingled. A distinction is made essentially between hydrophilic gels and hydrophobic gels. The latter are also known as oleogels. Oleogels are based on a nonpolar liquid, e.g., an oil, a wax or a paraffin, to which a gel-forming agent is added to achieve the desired physical properties.

Such oleogels may fulfill a variety of functions, depending on the composition.

Oleogels are used for topical application, in particular in the pharmaceutical field. In these pharmaceutical oleogels, a gel-forming agent is present in the gel in addition to the pharmaceutically active ingredients. Highly dispersed silicon dioxide, available under the brand name Aerosil®, is a widely used gel-forming agent for pharmaceutical oleogels. Oleogels are strongly thixotropic, i.e., they liquefy as a result of mechanical action and then solidify again. Other gels, e.g., gels containing pectin as the gel-forming agent, crosslink under the influence of an acid, while yet others undergo gelation as a function of temperature, e.g., gelatins.

Oleogels are also used industrially. An example is nonpolar coating agents (dripless paints). Highly dispersed silicon dioxide may also be used as the gel-forming agent for these applications. For industrial applications, this mineral gel-forming agent has the disadvantage that it does not burn without ash formation in thermal utilization of a product treated with such an oleogel.

Accordingly, it would be desirable to provide an oleogel-forming agent which is pharmaceutically active itself and burns without ash formation, an oleogel having such a gel-forming agent and a method for producing an oleogel having such a gel-forming agent.

SUMMARY OF THE INVENTION

An oleogel-forming agent according to an embodiment of the present invention has at least one highly dispersed triterpene.

Triterpenes such as betulin, lupeol, betulinic acid, oleanolic acid, and similar compounds are renewable raw materials that occur in the bark of the birch tree, for example. Betulin, betulinic acid, lupeol, and oleanolic acid are pentacyclic triterpenes, namely the first three having a lupane structure and the last having an oleanane structure. The characteristic feature of the lupane group is a ring having five carbons within the pentacyclic system which has an α-isopentenyl group in position $C_{19}$.

A method for producing triterpenes from plant parts, in particular betulin from birch bark, is described in WO 2001/72315 A1 and WO 2004/016336 A1, for example.

The pharmacological properties of triterpenes, in particular betulin, make the triterpene-containing oleogel-forming agent according to the present invention particularly interesting for the production of cosmetic and pharmaceutical oleogels.

The antiseptic properties of betulin were demonstrated as early as 1899, so it was used for sterilizing wound dressings and bandages (J. Wheeler (1899), Pharm. J., Die Darstellung des Betulin durch Sublimation [Synthesis of betulin by sublimation], 494, Ref. Chem. Centr. 1900 I, p. 353).

Furthermore, an anti-inflammatory effect similar to that of cortisone as well as a cytostatic effect have been demonstrated for betulin and betulin derivatives when used on various tumor cell lines in vitro (M. Carmen Recio et al. (1995), Investigations on the steroidal anti-inflammatory activity of triterpenoids from *Diospyros leucomelas*, Planta Med. 61, pp. 9-12; K. Yasukawa et al. (1991), Sterol and triterpene derivates from plants, Oncogene 48, pp. 72-76).

An antiviral action of betulin against herpes simplex viruses is described in U.S. Pat. No. 5,750,578. US 2002/0119935 A1 describes the action of triterpenes on bacterial infections and US 2002/0128210 A1 describes the action of triterpenes on fungal infections.

The average particle size of the at least one triterpene in the oleogel-forming agent is preferably less than 50 µm. The average particle size is particularly preferably less than 10 µm or even less than 100 nm to achieve excellent gel-forming properties. In this context we speak of a fine dispersivity if the particle size is between 100 nm and 10 µm and colloidal dispersivity if the particle size is between 1 nm and 100 nm.

The amount of secondary agglomerates of the at least one triterpene in the oleogel-forming agent preferably is less than 20% by weight. Ideally there is a homogeneous particle size distribution, i.e., a normal distribution of the frequency of individual particle sizes. The presence of secondary agglomerates may have a negative effect on the gel-forming properties of a powder, as suggested by the article by Knop, Reimann: "Kolloidale Kieselsäuren als Gelbildner" [Colloidal silicas as gel-forming agents], GOVI Verlag [GOVI Publishers], 2001.

The specific surface area of this triterpene may also have effects on the properties of the at least one highly dispersed triterpene as an oleogel-forming agent. Experiments have shown that gel-forming properties are improved with an increase in specific surface area. This specific surface area of the at least one triterpene is in one embodiment between 1 $m^2/g$ and 500 $m^2/g$ and is preferably between 10 $m^2/g$ and 100 $m^2/g$ and particularly preferably between 20 $m^2/g$ and 50 $m^2/g$.

In addition to triterpenes such as betulin, betulinic acid, lupeol or allobetulin, the oleogel-forming agent in the form of a micronized triterpene-containing powder may also contain a small amount of other substances, e.g., those substances that are also present naturally in a certain amount in triterpene-containing plant parts, e.g., birch bark from which triterpenes may be extracted. The triterpene content in the oleogel-forming agent according to the present invention is preferably more than 80% by weight, particularly preferably more than 90% by weight, based on the weight of the oleogel-forming agent. The betulin content is advantageously more than 80% by weight, based on the triterpene content.

The triterpene-containing oleogel-forming agent according to the present invention may also be used for industrial applications, e.g., in nonpolar coating agents. It has the advantage for such applications that it burns without ash formation in thermal utilization—unlike mineral gel-forming agents.

The oleogel according to an embodiment of the present invention contains:

a nonpolar liquid in a proportion between 80% by weight and 99% by weight, based on the total weight of the gel and the above mentioned triterpene-containing oleogel-forming agent as the gel-forming agent in a proportion between 1% by weight and 20% by weight, preferably between 3% by weight and 15% by weight, particularly preferably between 6% by weight and 12% by weight, based on the total weight of the gel.

The advantage of this semisolid preparation in the form of an oleogel lies in the simplicity of its formulation, whereby the triterpene functions simultaneously as a pharmaceutically active substance and as a gel-forming agent, so that no additional gel-forming agents need to be used. The oleogel is therefore particularly suitable for allergy-prone skin.

Using the triterpene-containing highly dispersed, preferably finely dispersed or colloidally dispersed powder mentioned above as the oleogel-forming agent having a triterpene content in the concentration range as indicated and having the stated average particle size, it is possible to produce a gel which does not contain any other ingredients in addition to the at least one pharmaceutically active triterpene which is present in powder form and the nonpolar liquid. Triterpenes have a solubility of less than 0.5% in nonpolar liquids, so the triterpenes are present primarily in the form of undissolved solid particles in the gel.

However, there is of course also the possibility of adding other pharmaceutically active substances to the oleogel in addition to the triterpene present in the gel-forming agent.

The advantages of an oleogel with a triterpene-containing oleogel-forming agent are varied, depending on the area of use.

A novel semisolid preparation is thus made available for the cosmetic pharmaceutical field. It is good in particular on dry skin and on the lips in comparison with preparations containing water. Topical use of the oleogel according to the present invention is advantageous in particular for people at risk of allergies because no other gel-forming agents are necessary. On the other hand, the oleogel may also be used as an additive-free pharmaceutical base into which other lipophilic and, using water, also hydrophilic active ingredients or excipients may be easily incorporated.

A thixotropic composition having a nonmineral oleogel-forming agent which therefore burns without ash formation is made available for the industrial field. For example, nonpolar coating agents (dripless paints) having an increased thixotropy thanks to the oleogel-forming agent according to the present invention constitute one area of application. The gel-forming agent also has the antiseptic properties and light-stabilizing effects known for triterpenes.

The proportion of nonpolar liquid in the oleogel is preferably between 88% by weight and 94% by weight and the amount of triterpene-containing powder is preferably between 6% by weight and 12% by weight.

Any nonpolar liquids such as vegetable, animal or synthetic oils, waxes, and paraffins are suitable as the nonpolar liquid for the oleogel. The nonpolar liquid is, for example, a vegetable oil such as sunflower oil, olive oil, avocado oil, almond oil, or a mixture of these oils.

The oleogel according to the present invention has a viscosity that has only a slight dependence on temperature, but it has a strong thixotropic behavior so that the gel is simple to store and use.

The oleogel-forming agent in the form of the highly dispersed, preferably finely dispersed or colloidally dispersed triterpene powder may also be used as a thickener if it is used in the liquid to be thickened in a concentration below the gelation limit, i.e., the concentration that would be necessary to form an oleogel from the liquid and the triterpene.

There is the possibility of adding the highly dispersed triterpene to the nonpolar liquid in a concentration that is below the gelation limit, i.e., below the concentration required for gelation. The result is an oleosol, i.e., a viscous preparation, in which the highly dispersed, preferably finely dispersed, or colloidally dispersed triterpene acts as a thickener.

BRIEF DESCRIPTION OF THE DRAWINGS

The present invention is explained in greater detail below on the basis of an exemplary embodiment with reference to the attached FIGURE, in which:

The FIGURE shows a histogram and table values related to particle size distribution and frequency distribution of a sample of a highly dispersed oleogel-forming agent according to an embodiment of the invention.

DETAILED DESCRIPTION OF VARIOUS EMBODIMENTS

The top part of the FIGURE is a histogram illustrating the homogeneous particle size distribution of a sample of a highly dispersed oleogel-forming agent according to the present invention. The measured values on which the curve is based are shown in the form of a table in the bottom part of the FIGURE. A value for the frequency distribution in the right-hand part of the table is based on an interval of two particle sizes which are shown in the left part of the table with an offset in the upper and lower directions for the respective frequency value. The table thus indicates, for example, that the amount of particles having a size between 0.209 µm and 0.240 µm in the sample investigated is 0.14%.

The particle sizes of the sample are between 0.2 µm and 60.2 µm with the maximum size distribution being between 2.5 µm and 5 µm.

The distribution of particle sizes for the sample investigated is almost homogeneous, i.e., the frequency of the distribution increases steadily for diameters less than the maximum, which is approximately 3.5 µm, and decreases steadily for diameters greater than the maximum. The frequency increases again somewhat only for particles between approximately 34 µm and 45 µm in size. This increase might be attributable to secondary agglomerates, i.e., accumulations of particles formed only after the actual crystallization or formed by agglomeration of two or more crystals that initially crystallize independently of one another.

According to gas chromatographic analysis, this powder contains 85% by weight betulin, 5% by weight betulinic acid, 3% by weight oleanolic acid, 0.7% by weight lupeol, and 6.3% by weight other triterpene derivatives.

Using this highly dispersed powder as a gel-forming agent, an oleogel was produced by mixing the powder with 9% by weight sunflower oil, based on the total weight of the oleogel. The result was a stable semisolid gel with a very strong thixotropic behavior.

The oleogel produced in this way is suitable for treatment of a wide variety of skin diseases in humans and animals. Examples include actinic keratoses and basalioma in humans and mastitis in mammals.

The powder containing at least one triterpene and being active as an oleogel-forming agent may be obtained from plant parts by any traditional extraction methods. If the powder obtained by such extraction methods does not have the dispersibility, average particle size, and homogeneous particle size distribution required for the gel-forming properties, then the powder may be subjected to various procedures to arrive at the desired particle size, homogeneity, and dispersibility. Various methods for this, some of which are explained briefly below, are known to those skilled in the art who are trained in this field.

If the particle size in the powder is too high, impact or gravitation methods are suitable for reducing the size of the particles.

In addition, there is the possibility of dissolving the powder in a suitable solvent, e.g., tetrahydrofuran (THF) and subsequent recrystallization. This crystallization may be accomplished by spray drying or by cooling a saturated solvent, for example. The particle size may be adjusted via the crystallization conditions. In spray drying, for example, the crystallization conditions depend on the diameter of the nozzle through which the triterpene-solvent mixture is sprayed and on the temperature and pressure in the chamber into which the mixture is sprayed. In crystallization by cooling a saturated solution, the crystallization conditions depend on the temperature gradient over time during cooling and on the triterpene concentration in the solution.

It has been found that particularly small triterpene particles having a large specific surface area may be obtained by adding cold solvent to a saturated triterpene-solvent-mixture. This admixture of cold solvent results in cooling of the solution, causing the triterpenes to crystallize out. At the same time, the added cold solvent decreases the triterpene concentration in the solvent, with the result that small crystals tend to be formed, which is advantageous from the standpoint of the gel-forming properties.

Finally, there is also the possibility of sizing an existing powder to obtain a powder having the desired size distribution.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

The invention claimed is:

1. A method for producing a triterpene-containing oleogel, comprising:
    forming an oleogel using at least one highly dispersed triterpene having an average particle size of less than 50 µm that acts as an oleogel-forming agent in the oleogel, wherein the at least one highly dispersed triterpene is the only oleogel-forming agent in the oleogel.

2. The method as recited in claim 1, wherein the average particle size of the at least one triterpene is less than 10 µm.

3. The method as recited in claim 1, wherein the proportion of secondary agglomerates of the at least one triterpene is less than 20% by weight.

4. The method as recited in claim 3, wherein the at least one triterpene has a homogeneous particle size distribution.

5. The method as recited in claim 1, wherein the specific surface area of the at least one triterpene is between 1 $m^2/g$ and 500 $m^2/g$.

6. The method as recited in claim 5, wherein the specific surface area of the at least one triterpene is between 10 $m^2/g$ and 100 $m^2/g$.

7. The method as recited in claim 6, wherein the specific surface area of the at least one triterpene is between 20 $m^2/g$ and 50 $m^2/g$.

8. The method as recited in claim 1, wherein the amount of the at least highly dispersed triterpene is more than 80% by weight.

9. The method as recited in claim 8, wherein the proportion of the at least one highly dispersed triterpene is more than 90% by weight.

10. The method as recited in claim 1, wherein the at least one triterpene has a proportion of more than 80% by weight betulin.

* * * * *